US012712084B2

(12) United States Patent
Tai

(10) Patent No.: US 12,712,084 B2
(45) Date of Patent: Aug. 18, 2026

(54) INFECTIOUS DISEASE-MONITORING SMART DEVICE

(71) Applicant: SEOUL NATIONAL UNIVERSITY R&DB FOUNDATION, Seoul (KR)

(72) Inventor: Joo Ho Tai, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 318 days.

(21) Appl. No.: 18/270,371

(22) PCT Filed: Dec. 1, 2021

(86) PCT No.: PCT/KR2021/018015
§ 371 (c)(1),
(2) Date: Dec. 25, 2023

(87) PCT Pub. No.: WO2022/145757
PCT Pub. Date: Jul. 7, 2022

(65) Prior Publication Data

US 2025/0285770 A1 Sep. 11, 2025

(30) Foreign Application Priority Data

Dec. 29, 2020 (KR) ........................ 10-2020-0185840

(51) Int. Cl.
*G16H 50/80* (2018.01)
*G02B 27/00* (2006.01)
(Continued)

(52) U.S. Cl.
CPC ......... *G16H 50/80* (2018.01); *G02B 27/0093* (2013.01); *G02B 27/017* (2013.01); (Continued)

(58) Field of Classification Search
None
See application file for complete search history.

(56) References Cited

U.S. PATENT DOCUMENTS 11,342,051 B1 * 5/2022 Jain ........................ G16H 10/60
11,428,955 B1 * 8/2022 Lewis .................... G02C 7/083
(Continued)

FOREIGN PATENT DOCUMENTS

KR 20150014616 A 2/2015
KR 20170053145 A 5/2017
(Continued)

OTHER PUBLICATIONS

Younis et al., A Smart Context-Aware Hazard Attention System to Help People with Peripheral Vision Loss, Sensors 2019, 19(7), 1630 (Year: 2019).*

(Continued)

*Primary Examiner* — Anne-Marie K Alderson
(74) *Attorney, Agent, or Firm* — STIP Law Group, LLC

(57) ABSTRACT

The present invention relates to an infectious disease-monitoring smart device which provides information about the risk of infectious disease in real time and, specifically, to a smart device which enables a user to identify, through a device such as smart glasses, a location (e.g., a confirmed case's location or travel route) at which the risk of infectious disease exists, and further enables the user to obtain various information so as to respond to the above infectious disease in real time.

6 Claims, 11 Drawing Sheets

(51) Int. Cl.
*G02B 27/01* (2006.01)
*H04W 4/02* (2018.01)
*H04W 4/12* (2009.01)

(52) U.S. Cl.
CPC ............. *H04W 4/023* (2013.01); *H04W 4/12* (2013.01); *G02B 2027/0138* (2013.01); *G02B 2027/0178* (2013.01)

(56) References Cited

U.S. PATENT DOCUMENTS 11,504,011 B1 * 11/2022 Jain .......................... G06N 5/04
2013/0229289 A1 * 9/2013 Bensoussan ............. B60Q 1/52 340/902
2015/0100330 A1 * 4/2015 Shpits .................... G16H 50/80 705/2
2016/0080163 A1 * 3/2016 Taylor ................... H04W 4/024 370/312
2016/0136882 A1 * 5/2016 Cobbett ................. G16H 20/30 156/218
2017/0350702 A1 * 12/2017 Balasubramanian .... A61B 5/01
2017/0354883 A1 * 12/2017 Benedetto ........... A63F 13/5258
2018/0113508 A1 * 4/2018 Berkner-Cieslicki ........................ G06F 3/013
2020/0020162 A1 * 1/2020 Jones ..................... G01C 21/20
2021/0082199 A1 * 3/2021 Bonang ................... G06F 3/012
2021/0150874 A1 * 5/2021 Turano ................... G08B 21/12
2021/0158966 A1 * 5/2021 Ozaki .................... G16H 50/30
2022/0157474 A1 * 5/2022 Gurpur .................. G16H 50/30
2022/0178712 A1 * 6/2022 Marinescu ......... G01C 21/3461

FOREIGN PATENT DOCUMENTS

KR 101790755 B1 10/2017
KR 101806521 B1 12/2017
KR 101873805 B1 7/2018
KR 102128894 B1 7/2020
KR 102159722 B1 9/2020

OTHER PUBLICATIONS

International search report of PCT/KR2021/018015, Mar. 7, 2022, English translation.

* cited by examiner

FIG. 1

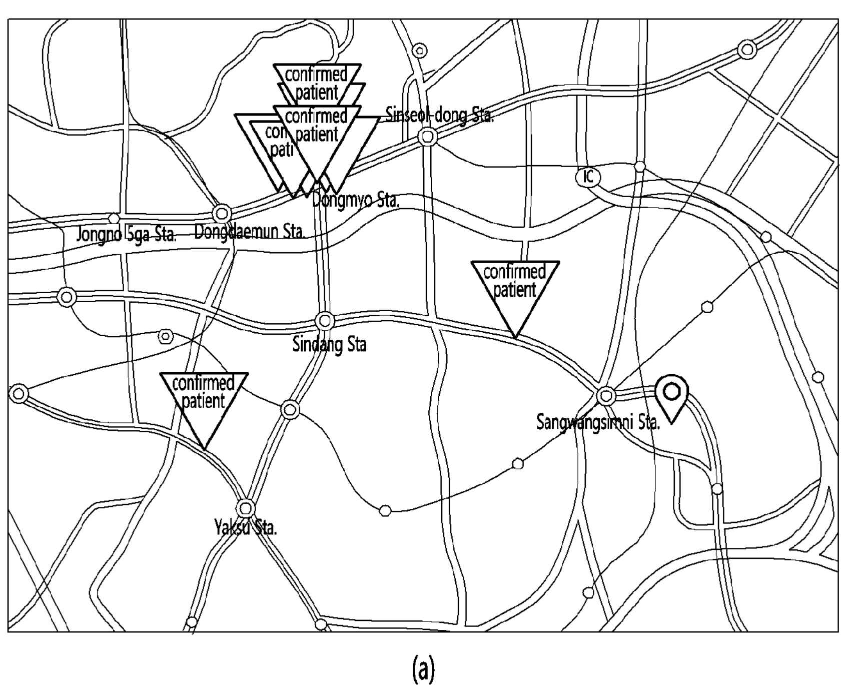

(a)

| DATE & TIME OF EXPOSURE | DISTRICT | COMPANY NAME | ADDRESS | DATE OF DISINFECTION | MASK WEARING |
|---|---|---|---|---|---|
| 07-18(SA) ~ 07-19(SU) | SEO-GU | HOME | CONTACT ID COMPLETED | 07-23 | - |
| 07-20(MO) 09:10-10:30 10:55-12:00 12:00-17:50 | SEO-GU | OFFICE | CONTACT ID COMPLETED | 07-24 | O |
| 07-20(MO) 10:30-10:45 | - | OO GAS STATION | CONTACT ID COMPLETED | 07-24 | O |
| 07-20(MO) 11:55-12:18 | SEO-GU | HAEGWANG RESTAURANT | 204-15, DONGNIM-RO SEO-GU | 07-24 | X |
| 07-20(MO) 18:05-18:27 | SEO-GU | OO MART | CONTACT ID COMPLETED | 07-24 | O |
| 07-20(MO) 18:36-18:41 | SEO-GU | OOO RESTAURANT | CONTACT ID COMPLETED | 07-24 | O |
| 07-21(TU) | SEO-GU | HOME | CONTACT ID COMPLETED | 07-23 | - |
| 07-22(WE) 10:35-10:40 | SEO-GU | OOO HOSPITAL | CONTACT ID COMPLETED | 07-24 | O |
| 07-22(WE) 10:42-10:43 | SEO-GU | OOO PHARMACY | CONTACT ID COMPLETED | 07-24 | O |
| 07-22(WE) 10:56-10:58 | SEO-GU | OOO RESTAURANT | CONTACT ID COMPLETED | 07-24 | O |
| 07-23(TH) 14:30-15:00 | SEO-GU | SCREENING CLINIC | - | - | O |

Figure 4:
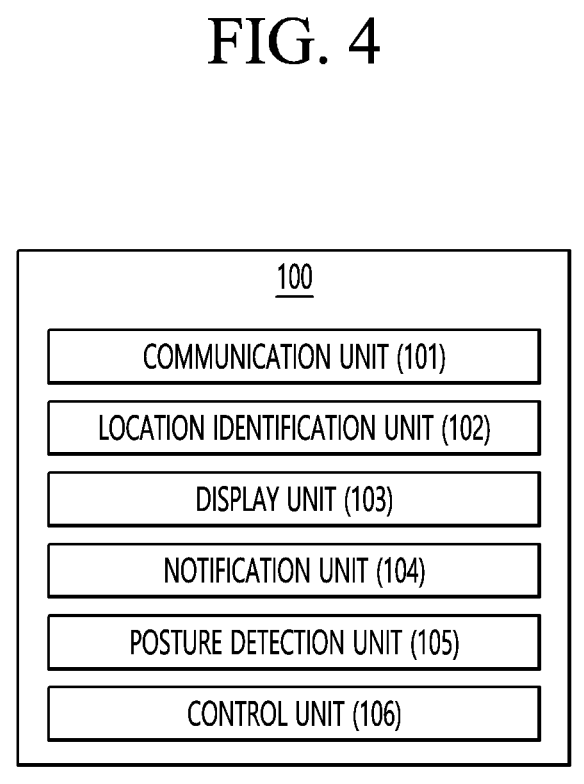

COMMUNICATION UNIT (101)

LOCATION IDENTIFICATION UNIT (102)

DISPLAY UNIT (103)

NOTIFICATION UNIT (104)

POSTURE DETECTION UNIT (105)

CONTROL UNIT (106)

FIG. 8
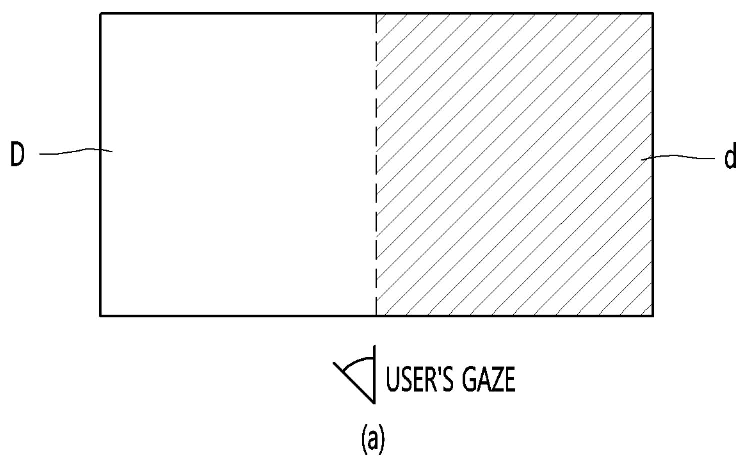
(a)
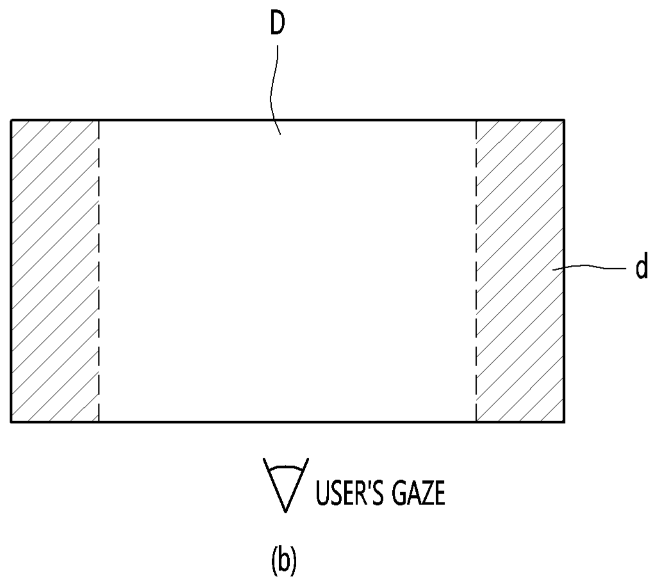
(b)

INFECTIOUS DISEASE-MONITORING SMART DEVICE

CROSS-REFERENCE TO RELATED APPLICATIONS

This application is the U.S. National Phase under 35 U.S.C. § 371 of International Application No. PCT/KR2021/018015, filed on Dec. 1, 2021, which in turn claims the benefit of Korean Application No. 10-2020-0185840, filed on Dec. 29, 2020, the disclosures of which are incorporated by reference into the present application.

TECHNICAL FIELD

The present disclosure relates to an infectious disease-monitoring smart device that provides a danger of an infectious disease in real time, and more particularly, a smart device that allows a user to identify a dangerous location of an infectious disease (e.g., a location of a confirmed infectious disease patient and a predetermined range from the location, or a movement thereof) through a device such as smart glasses, or to monitor the movement of a marked tracking target, and moreover, to obtain various information so as to respond to the above infectious disease in real time.

BACKGROUND ART

Starting with the 1918 bird flu, to SARS from civet cats, MERS through bats and camels, and recently to the COVID-19 virus transmitted from bats again, damages caused by new disaster-type infectious diseases mainly transmitted from animals to humans have been very large, and social and economic damages caused by them continue to increase throughout the world. Looking at the cases of animal infectious diseases as well as the COVID-19, a large number of pigs were slaughtered due to African swine fever just a few months ago, and many animals are still exposed to the danger of infectious diseases at this point.

On the other hand, in order to resolve the spread of damages caused by these infectious diseases, it is most desirable to block the transmission of infectious diseases from humans or animals to other individuals, but there is a limit to controlling many humans or animals at once. Accordingly, in recent years, more attempts have been made to prevent non-infected individuals from approaching the vicinity of infected individuals, and as part of this, there is a spread of an application that informs a movement of a confirmed patient.

The application that informs a movement of an infected person is evaluated as a great help to general users, but in the case of the application in the related art, it is limited to simply showing the movement of the infected person as a list or simply displaying the above list on a map, and thus unable to provide three-dimensional information to the user.

The present disclosure relates to a user-centered infectious disease-monitoring smart device capable of providing various information so as to allow a non-infected user to prevent an infectious disease or an infected user to prevent the infectious disease to others. On the other hand, the present disclosure is derived in view of the foregoing problems to resolve the above-mentioned technical problems, as well as to provide additional technical elements that cannot be easily invented by those skilled in the art.

DISCLOSURE OF INVENTION

Technical Problem

An aspect of the present disclosure is to mainly allow a user who is not suffering from an infectious disease or users who want to find a suspected infection, an infected person, an infected animal itself or a causative factor to dynamically identify a location where the infectious disease is in danger, that is, a disease location of a confirmed infectious patient, a predetermined range or radius from the location, and a movement thereof in real time through a smart device.

In particular, another aspect of the present disclosure is to allow multiple users to be easily informed of the danger of an infectious disease in front of their eyes by using smart glasses.

On the other hand, technical problems of the present disclosure may be not limited to the above-mentioned problems, and other technical problems which are not mentioned will be clearly understood by those skilled in the art from the following description.

Solution to Problem

In order to solve the foregoing problems, there is provided a method of providing information for infectious disease monitoring using a smart device according to an embodiment of the present disclosure, the method including receiving infectious disease transmission information from a service server; acquiring current location information of the smart device, and displaying at least one of a dangerous path or a dangerous location included in the infectious disease transmission information through a display provided in the smart device with reference to the acquired current location information; and comparing the current location information with the infectious disease transmission information to output a notification to a user.

Furthermore, in the method of providing information for infectious disease monitoring using a smart device, the smart device may receive infectious disease transmission information at preset time intervals from the service server, and the smart device may be smart glasses.

Furthermore, in the method of providing information for infectious disease monitoring using a smart device, the smart glasses may further include a gaze sensor that tracks a user's gaze, and the smart glasses may output a predetermined notification when it is detected that the user's gaze is directed toward a front center thereof.

Furthermore, in the method of providing information for infectious disease monitoring using a smart device, the outputting through the display may be displaying and outputting at least one of a dangerous path and a dangerous place included in the infectious disease transmission information on a video photographed through a photographing unit provided in the smart glasses.

Furthermore, in the method of providing information for infectious disease monitoring using a smart device, the dangerous path may include a travel path of a confirmed patient or a travel path of another user who has traveled on a path at least part of which overlaps the travel path of the confirmed patient.

Furthermore, in the method of providing information for infectious disease monitoring using a smart device, the notification may vary an output method thereof according to a distance from the dangerous path or dangerous place based on current location information acquired in real time.

On the other hand, there is provided a method of providing information for infectious disease monitoring using a smart device according to another embodiment of the present disclosure, the method including identifying a marker in a video photographed through a photographing unit provided in the smart device; setting an individual marked with the marker as a tracking target; and marking the tracking target in a video photographed through the photographing unit to display the marked tracking target through a display provided in the smart device.

On the other hand, there is provided an infectious disease-monitoring smart device according to still another embodiment of the present disclosure, including a communication unit that receives infectious disease transmission information from a service server; a location identification unit that acquires a current location of the smart device; a display unit that displays at least one of a dangerous path or a dangerous place included in the infectious disease transmission information with reference to current location information acquired by the location identification unit; a notification unit that compares the current location information with the infectious disease transmission information to output a notification to a user; and a control unit that controls the communication unit, the location identification unit, the display unit, and the notification unit.

In addition, there is provided an infectious disease-monitoring smart device, including a photographing unit that photographs a forward field-of-view; a display unit that displays and outputs a tracking target in a video photographed by the photographing unit; and a control unit that controls the photographing unit and the display unit, wherein the control unit identifies a marker in an video photographed by the photographing unit to set an individual marked with the marker as a tracking target.

On the other hand, there is provided a method of providing information for infectious disease monitoring using a smart device, the method including identifying a marker in a video photographed through a photographing unit of the smart device; setting an individual marked with the marker as a tracking target; and displaying the tracking target to be distinguished from other objects within the video.

Furthermore, the method of providing information for infectious disease monitoring using a smart device may further include determining a state of a tracking target based on parameters—the parameters include a body temperature or behavior pattern of the tracking target-acquired from the tracking target in the video using an artificial intelligence algorithm.

Advantageous Effects of Invention

According to the present disclosure, there is an effect in that users may receive infectious disease transmission information in real time, and in particular, easily know paths traveled (dangerous paths) or places visited (dangerous places) by confirmed infectious disease patients, and a dangerous radius or dangerous range predicted therefrom.

Furthermore, according to the present disclosure, a dangerous path, a dangerous location, a dangerous radius, or a dangerous range included in infectious disease transmission information may be provided in real time through smart glasses, similar to a navigation interface, thereby having an effect of allowing a user to easily avoid a dangerous source of the infectious disease.

In addition, according to the present disclosure, local location information on a smart device may be compared with infectious disease transmission information received from an external service server, and then how close a current location is to a dangerous source of the infectious disease may be identified and informed to a user, thereby having an effect of allowing the user to more easily avoid the dangerous source of the infectious disease.

Moreover, according to the present disclosure, a means for detecting a specific component contained in droplets may be provided in a smart device by itself, thereby having an effect of allowing a user to recognize it when in contact with a person having an infectious disease.

Besides, according to the present disclosure, a smart device may identify a specific marker—the marker is displayed on a specific target object—and define an individual marked with the marker as a tracking target, thereby having an effect of allowing a user to easily find the tracking target using the smart device.

Meanwhile, the effects according to the present disclosure are not limited to those mentioned above, and it is understood that there are other technical effects within a range in which those skilled in the art can infer.

BRIEF DESCRIPTION OF DRAWINGS

FIG. 1 shows a state in which a travel path of a confirmed infectious disease patient has been previously guided.

FIG. 4 shows a detailed configuration of a smart device according to the present disclosure.

FIG. 8 shows a state in which infectious disease transmission information is displayed differently on a display according to a result of tracking a user's gaze.

MODE FOR THE INVENTION

Figure 2:
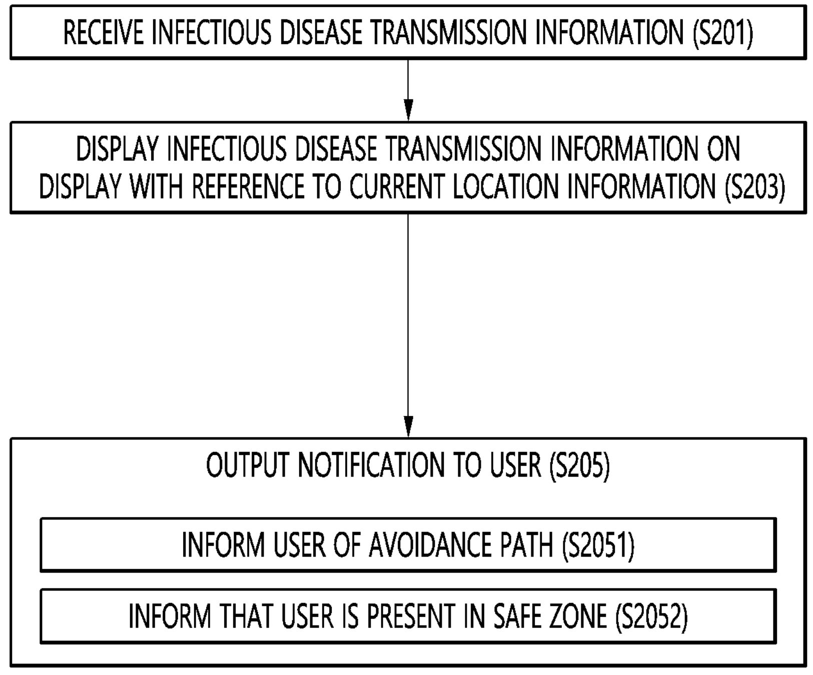
FIG. 2 shows a process in which a method according to a first embodiment of the present disclosure is carried out in sequence.

Details of objects and technical configurations of the present disclosure and the resultant operational effects will be more clearly understood by the following detailed description based on the accompanying drawings herein. An embodiment according to the present disclosure will be described in detail with reference to the accompanying drawings.

The embodiments disclosed herein should not be construed or used to limit the scope of the present disclosure. It will be appreciated for those skilled in the art that the description, including the embodiments herein, has various applications. Therefore, any embodiments described in the detailed description of the present disclosure are exemplary to better describe the present disclosure, and the scope of the present disclosure is not intended to be limited to the embodiments.

The functional blocks shown in the drawings and described below are only examples of possible implementations. Other functional blocks may be used in other implementations without departing from the concept and scope of the detailed description. Furthermore, although one or more functional blocks of the present disclosure are shown as separate blocks, one or more of the functional blocks of the present disclosure may be combinations of various hardware and software configurations that perform the same function.

In addition, the expression that includes certain elements is an open-type expression and merely refers to existence of the corresponding elements, and should not be understood to exclude additional elements.

Moreover, it should be understood that when an element is referred to as being "connected" or "coupled" to another element, the element can be directly connected or coupled to the other element or intervening elements may be present.

First, FIG. 1 shows a state in which a path traveled by a confirmed infectious diseases patient is displayed in a table or on a map, wherein, in particular, it can be seen that only minimal information, text or links such as places (company names) through which the confirmed patient has passed, dates and times of exposure are provided as a notification according to the table provided with the travel path, and there is inconvenience in that the information is very limited even though displayed on the map, so ordinary citizens may only roughly identify that the confirmed patient has been present at a certain place in a certain zone, but may not be able to know more specific information.

In the meantime, some citizens may inevitably have to work or visit within a zone where the confirmed case has occurred, and in such a situation, the citizens cannot help but feel great anxiety when visiting the zone.

The present disclosure is intended to improve an environment that previously has limited a travel path of a confirmed patient, and an aspect of the present disclosure is to collect or receive infectious disease transmission information from a central service server in all directions, and to provide it to a user with reference to the collected information, but if necessary, to generate additional information based on the collected information and provide the user with more practically necessary information for infectious disease monitoring.

FIG. 2 shows a flowchart in which a method of the first embodiment according to the present disclosure is listed in sequence, and according to the method, the first embodiment largely includes receiving infectious disease transmission information from a service server (S201), acquiring a current location information of the smart device, and displaying at least one of a dangerous path or a dangerous place included in the infectious disease transmission information through a display provided in the smart device with reference to the acquired current location information (S203), and comparing the current location information with the infectious disease transmission information to output a notification to a user (S205). For reference, it will be understood that the outputting of a notification to the user (S205) covers all of outputting notifications with various content, and for example, a process of outputting an avoidance path to the user (S2051), and a process of notifying that the user is present in a safe zone (S2052), and the like may be included therein.

Prior to describing respective steps in FIG. 2, first, an outline of a system that is a premise for implementing the first embodiment will be described through FIG. 3, and a detailed configuration of a smart device through FIG. 4.

Figure 3:
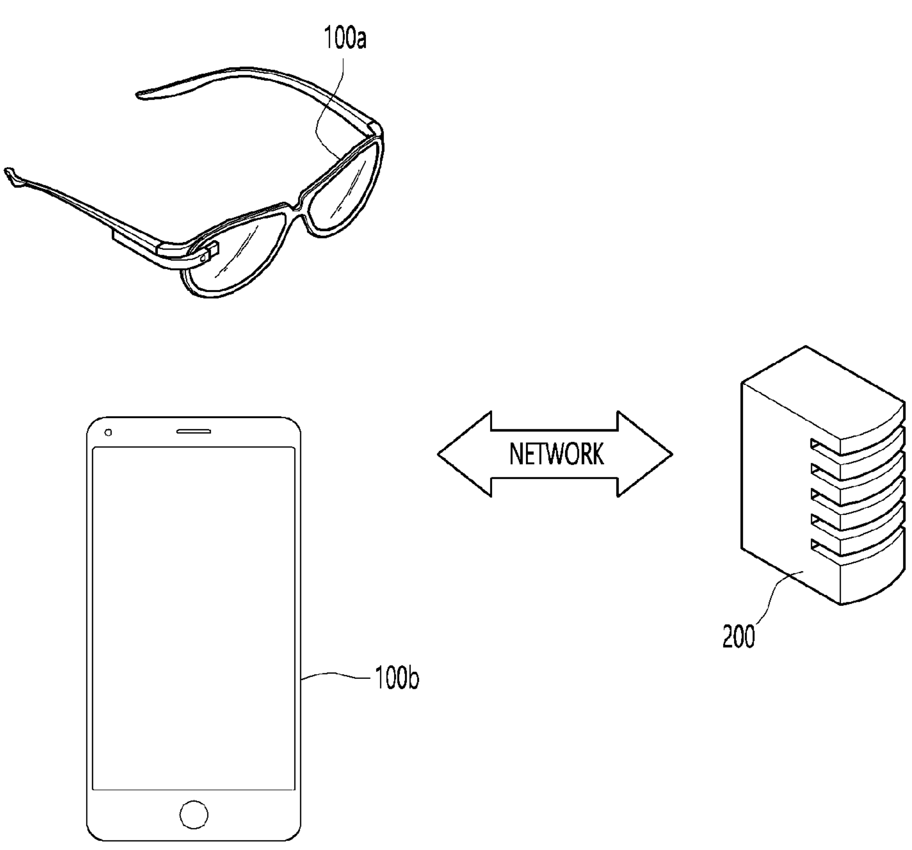
FIG. 3 shows a system that is a premise for implementing the first embodiment.

First, according to FIG. 3, the system may largely include a smart device and a service server.

A smart device, which is referred to as a device possessed or carried by a user, may include a portable terminal such as a smart phone, a PDA, a tablet PC, or the like, and furthermore, a wearable device such as smart glasses, a smart watch, or the like.

When the above smart devices are viewed in terms of hardware, it is assumed that each of the smart devices has a central processing unit (CPU) and a memory. The central processing unit may also be referred to as a controller, a microcontroller, a microprocessor, a microcomputer, and the like. Furthermore, the central processing unit may be implemented by hardware or firmware, software, or a combination thereof, and when the central processing unit is implemented using hardware, it may be configured as an application specific integrated circuit (ASIC) or a digital signal processor (DSP), a digital signal processing device (DSPD), a programmable logic device (PLD), or a field programmable gate array (FPGA), and when the central processing unit is implemented using firmware or software, the firmware or software may be configured to include a module, a procedure, a function or the like that performs functions or operations as described above. In addition, the memory may be implemented as read only memory (ROM), random access memory (RAM), erasable programmable read only memory (EPROM), electrically erasable programmable read-only memory (EEPROM), flash memory, static RAM (SRAM), a hard disk drive (HDD), a solid-state drive (SSD), or the like. For reference, in this detailed description, it will be mainly described on the assumption that the smart device is smart glasses to help the understanding of the present disclosure, but the present disclosure is not necessarily limited thereto.

Meanwhile, it will be understood that the service server is a component that provides s infectious disease transmission information toward the smart device to implement a method according to the present disclosure, and moreover, it will also be understood that the service server is a component that provides an application program allowing the smart device to be driven according to an embodiment according to the present disclosure (including a component that provides the application program by way of an application store). A type of service server may be at least one server PC managed by a specific operator, or a type of cloud server provided by another company, that is, a type of cloud server for allowing the operator to sign up for use. In particular, when the service server is implemented as a server PC, the corresponding service server may include a central processing unit and a memory, and this has been described in detail in the foregoing description of the smart device, and thus a description thereof will be omitted herein.

Meanwhile, FIG. 4 shows a detailed configuration of a smart device referred to in this detailed description, and according to the configuration, the smart device 100 may largely include a communication unit 101, a location identification unit 102, a display unit 103, and a control unit 106, and additionally, may further include a notification unit 104 and a posture detection unit 105.

First, the communication unit 101 is a component that receives infectious disease transmission information from the service server 200, and the communication unit 101 has no limitation on a network mean as long as it can be connected to a network that allows data transmission and reception with respect to an external service server.

The location identification unit 102, which is a component that acquires a current location of the smart device 100, may preferably acquire the current location using a GPS or Wi-Fi or Bluetooth beacon. For example, when the smart device 100 is present outdoors, location information may be measured from GPS satellites to allow GPS positioning, and if the smart device 100 is present indoors to disallow GPS positioning, then the location information of the smart device may be measured using the MAC address of a Wi-Fi provided nearby or a Bluetooth beacon. In addition, when the location information of the smart device 100 can be measured in any other method not mentioned herein, it can be used with no limitation.

Next, it will be understood that the display unit 103 is a component that outputs various information including infectious disease transmission information to the user, and there is no limitation to its display method as long as the user is able to view a series of information through his or her eyes on a smartphone or smart glasses. Through the display unit 103, an avoidance path may be displayed to allow the user to avoid and pass through an infectious disease danger zone, or information related to other infectious disease transmission information may be displayed.

It will be understood that the notification unit 104 is a component that notifies the user of the smart device 100 of a specific situation or event through sound, light, or vibration, and the above notification unit 104 may be implemented to operate when a preset condition is satisfied under the control of the control unit 106. For example, the notification unit 104 may operate a notification when the user approaches within a preset range from an infectious disease danger zone, or may operate a notification even when the user moves out of the infectious disease danger zone.

The posture detection unit 105, which is a component that senses which posture the smart device 100 is currently present in, and this component will be described in more detail in an embodiment related to smart glasses to be described later.

Finally, it will be understood that the control unit 106, which controls all of the above components, corresponds to the central processing unit mentioned above when describing the hardware of the smart device. Since the functions of the control unit correspond to those of the first embodiment mentioned in this detailed description, a detailed description of the functions of the control unit will be understood through the description of FIG. 2.

Hardware components required to implement the method according to the first embodiment have been described above through FIGS. 3 and 4.

Looking to the first embodiment with reference to FIG. 2 again, the first embodiment first starts with receiving, by the smart device, infectious disease transmission information from the service server (S201). Infectious disease transmission information may include all of a series of information on a current transmission situation of an infectious disease, such as a path traveled by a person who has been confirmed to have an infectious disease (confirmed patient), a place or address visited by the confirmed patient, and a time and period of exposure of the confirmed patient to the outside, other known personal information on the confirmed patient, and the like. Such infectious disease transmission information may be collected by a service server from servers operated by central other external servers (e. g., government agencies or servers operated by private organizations). Meanwhile, in the step S201, it is described that the smart device receives infectious disease transmission information from the service server, but it is not necessarily limited thereto, and the smart device may also be implemented to directly receive infectious disease transmission information from a server operated by a central government agency. In addition, it is preferably understood that the data transmission and reception itself in the step S201 is performed through the communication unit, but essentially, the communication unit is driven under the control of the control unit to receive the infectious disease transmission information.

Subsequent to the step S201, acquiring, by the smart device, current location information, and displaying at least one of a dangerous path or a dangerous place included in the infectious disease transmission information through a display provided in the smart device with reference to the acquired current location information (S203) may be carried out. In the smart device, the location information unit may be always activated, and through this, current location information of the smart device may be obtained in real time, and the current location information acquired in real time in this manner may be referenced to output infectious disease transmission information that has been previously received, more specifically, a travel path of a confirmed patient, or place information visited by the confirmed patient, or a travel path passed by any user with a history overlapping a movement of a certain confirmed patient, and the like, included in the infectious disease transmission information, on the display of the smart device. That is, the confirmed patient's travel path, the confirmed patient's visited place, or the travel path of an arbitrary user included in the infectious disease transmission information are basically based on location information, and as a result, the smart device may be implemented to compare current location information with location information included in the infectious disease transmission information to display only infectious disease transmission information in a surrounding region around the current location information.

Subsequent to step S203, the smart device may selectively control the notification unit to notify the user of a danger. For example, the control unit of the smart device may be implemented to control the notification unit when it is determined that a confirmed patient's travel path (dangerous path) or a confirmed patient's visited place (dangerous place) is present within a preset radius based on the current location information, thereby notifying it to the user. As a more specific example, assuming that the user is walking while carrying the smart device, when a dangerous path or dangerous place is present within a radius of 500 m from a current location, the smart device may be allowed to vibrate, blink a translucent red background color on the display of the smart device, or output a loud notification sound through a speaker, thereby notifying that the user is currently passing through a dangerous path or a dangerous place. A control condition of the notification unit may be implemented in more various ways, and for example, a sound, a red background color blinking cycle, a background color depth, or a strength of vibration may be increased as the current location of the smart device moves closer to a dangerous source (dangerous path or dangerous place), and conversely, the strength of the output may be decreased as moving away from the dangerous source, thereby inducing the user to move away from the dangerous source. Alternatively, when a current advancing direction of the smart device matches a dangerous path, a notification may be output, thereby inducing the user not to walk along the same path as a confirmed infectious disease patient has passed.

Figure 5:
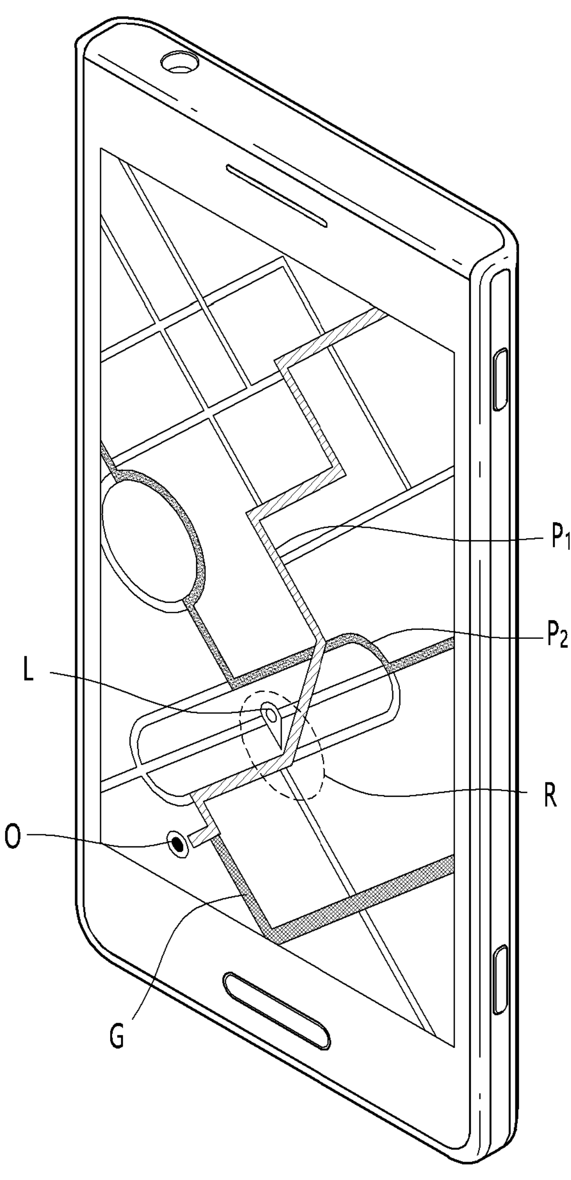
FIG. 5 conceptually shows an embodiment in which infectious disease transmission information is provided through a smart device from a user's point of view.

FIG. 5 schematically shows a state in which a user moves on foot while holding a smart device or wearing the device in the case of a wearable smart device, and in this case, a path for the user to go to a destination may be displayed on the smart device, and moreover, dangerous sources that are present around the path, that is, a travel path or visited places of a confirmed patient may be displayed together, thereby allowing the user to avoid them.

Meanwhile, the control unit of the smart device may also perform path guidance in addition to the above-mentioned functions. That is, the control unit of the smart device may compute a path from current location information to a destination subsequent to receiving the destination input from the user, and display a result of the computation on a display of the smart device. At this time, the control unit may generate and provide a path that does not pass through or does not overlap a dangerous place or a dangerous path to the user. In addition, the user may set a path to be generated such that no dangerous path or dangerous place is present in an arbitrary region, for example, within a radius of 200 m, through a separate user setting menu, and the control unit may compute and provide a path to a destination according to those settings to the user.

Referring to FIG. 5, a user's current location (O), a confirmed patient's travel path (P1), another user's travel path (P2) overlapping that of the confirmed patient—here, another user refers to a user who can share his or her location information as a person who uses a service according to the present disclosure —, a visited place (L) of the confirmed patient, an arbitrary dangerous region (R) based on the visited place of the confirmed patient, an avoidance path (G) provided to travel by avoiding the travel path of the confirmed patient, and the like may be displayed on the smart device. Among them, the dangerous region (R) is not necessarily displayed only in a circular shape, but may also be displayed in other shapes such as regular or irregular polygons.

Figure 6:
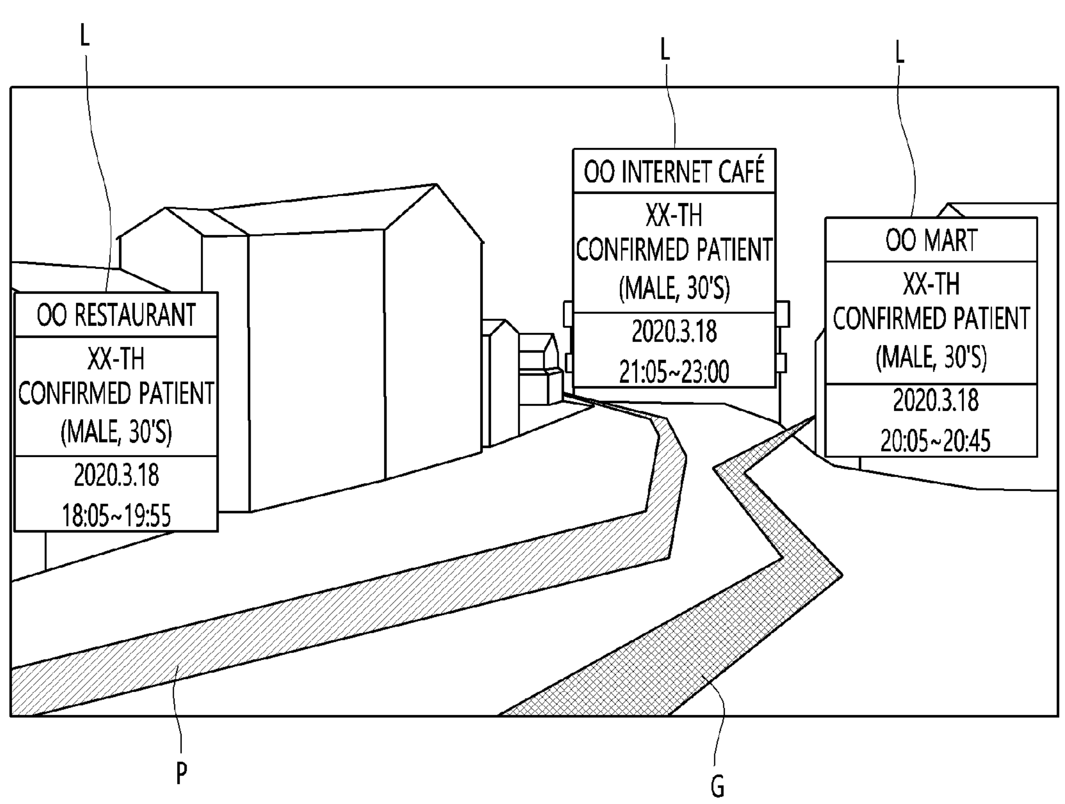
FIG. 6 shows a state in which infectious disease transmission information is provided when the smart device is smart glasses.
Figure 7:
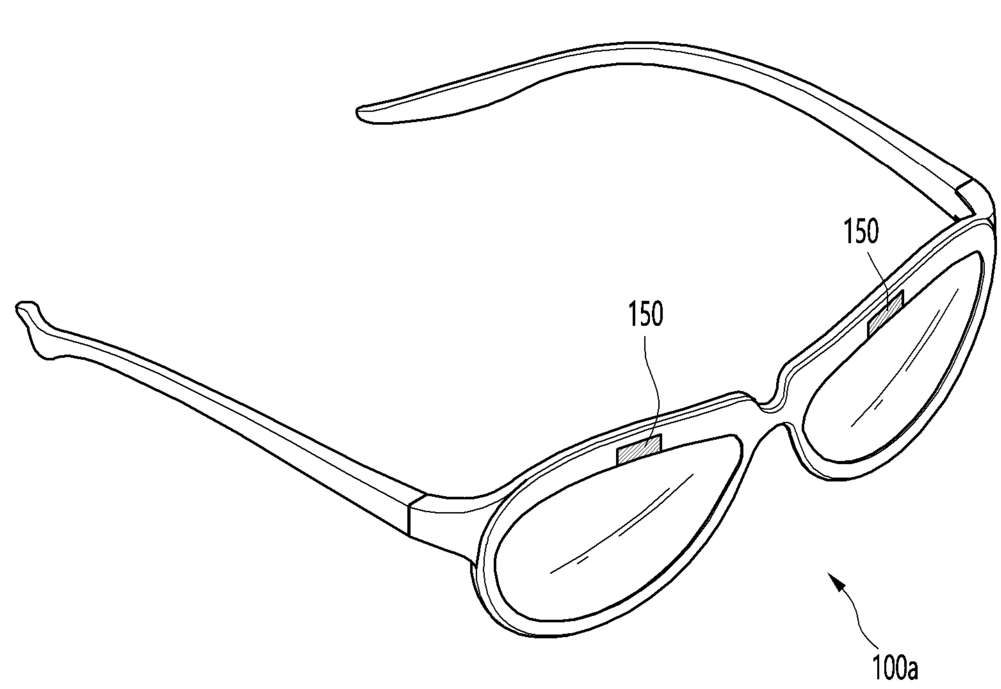
FIG. 7 shows an embodiment in which a sensor is provided in smart glasses to track a user's gaze.

Meanwhile, FIG. 6 shows a state in which infectious disease transmission information is provided through a display of smart glasses when the smart device according to the present disclosure is the smart glasses. Even when the smart device is smart glasses, it may include all of the specific components described above in FIG. 4, but may be different from a typical smartphone in such a manner that the display in the smart glasses outputs information on a lens to allow the user to visually see it. A smart device according to the present disclosure may preferably have functions and structures as shown in FIGS. 7 and 8 to be described later. However, although there may be many different methods to implement a display in smart glasses, it will be understood that the display in this detailed description covers all display methods that can be implemented when designing smart glasses.

In addition, in the case of smart glasses, a photographing unit capable of photographing a user's field-of-view direction in real time may be further included, and generally implemented as a camera for photographing a forward side, which is a direction in which the user is walking. The smart glasses worn by the user photograph a field-of-view (FOV) in the same direction as the user in real time, and a video or image photographed at this time may be used to provide another type of processed information to the user, and for example, the smart glasses may be used to recognize a sidewalk or road in the photographed video and display a path guide line thereon, or to recognize a specific building and display its related information thereon.

Referring again to FIG. 6, the drawing shows a panoramic view of a front street viewed from a gaze of the user who wears smart glasses, wherein it can be seen that infectious disease transmission information, for example, a dangerous path, which is a path passed by a confirmed patient or another user (hereinafter referred to as an overlapping confirmed patient) confirmed to have traveled on a path overlapping the confirmed patient's path, and a dangerous place visited by the confirmed patient or overlapping confirmed patient are displayed for the user to easily recognize them. That is, from the user's point of view, it may be implemented to be displayed as if navigation information is provided on smart glasses, and through this, the user may easily know whether a path he or she is currently walking overlaps the confirmed patient's travel path, or whether there are places where the confirmed patient has stopped in on his or her travel path, thereby allowing the user to continue moving while keeping a distance from those dangerous sources.

In addition, referring to FIG. 6, the display of the smart glasses may display not only a dangerous path or a dangerous place, but also a path to a destination that the user wants to go to. The path to the destination may be computed by the control unit 106 of the smart t glasses, and reference will be made to the above description of FIG. 5, for details on this.

Meanwhile, in addition to the detailed components mentioned in FIG. 4, the smart glasses may further include the posture detection unit 105. The posture detection unit 105, which is configured to measure parameters corresponding to a mechanical movement of the smart glasses, is basically based on a principle of measuring an angular movement with respect to an inertial space around one or more axes orthogonal to an internal spin axis. The posture detection unit 105 may allow to know which direction the smart glasses are currently facing, as well as a degree of rolling, yawing, and pitching of the smart glasses. The information acquired by the posture detection unit 105 of the smart glasses may be used to display more accurate information to the user on the display. For example, it has been described above that infectious disease transmission information (dangerous path, dangerous place, dangerous region, overlapping path, etc.) can be displayed on a video or image obtained by the photographing unit of the smart glasses, but in general, when adding new information to a video or image provided in this 1 manner, identifying objects (roads, buildings, etc.) included in the video or image using various graphic analysis methods, and then adding new information thereto is often carried out. However, using only such a pure graphic analysis method may impose a very large computational burden on the control unit 106, which may cause side effects such as slowing down speed and increasing resource consumption, thereby reducing the lifespan of the smart glasses. The posture detection unit 105 provided in the smart glasses may acquire information on which direction the smart glasses worn by the user are facing, so-called posture information, and this posture information may be referenced to generate information displayed on the display by the control unit 106. Illustratively, the control unit 106 may approximately know a direction of the field-of-view that is viewed through the smart glasses by primarily referring to the posture information, and then graphically analyze the video or image acquired by the photographing unit, thereby identifying roads, buildings, and the like within the field-of-view. For reference, a graphic analysis process of the control unit 106 may include a process of comparing the video or image with a pre-stored map database or 3D map database. As such, the posture detection unit 105 provided in the smart glasses may detect and provide posture information, thereby allowing infectious disease transmission information to be more quickly and accurately displayed.

Meanwhile, the smart glasses may further include a gaze sensor capable of tracking the user's gaze. The gaze sensor may also be provided to display infectious disease transmission information to the user at a more accurate location on the display of the smart glasses, and more specifically, it will be understood that the gaze sensor is provided to identify which direction the user's eyes are actually facing and then display infectious disease transmission information according to the direction. In a case where the smart glasses allow the user's gaze to be tracked, the smart glasses may be allowed to output an appropriate notification when the user's gaze is looking towards the center or when the user's gaze matches a direction of the center of the FOV, thereby allowing the user to view the path in a forward direction.

FIG. 7 shows a view in which a gaze sensor 150 is provided at a top of the lens in the smart glasses, and in this case, the gaze sensor 150 may be provided on a frame or lens surface of the smart glasses to track the movement of the pupil. In FIG. 7, it is shown that the gaze sensor 150 is provided at the top of the lens, but it will be understood that a location at which the gaze sensor is provided is not limited thereto.

As mentioned above, a function of the gaze sensor 150, which is to identify which direction the user's gaze is actually facing by sensing the direction of the user's gaze, may be used to display infectious disease transmission information, such as whether any dangerous path or place is present, and other warning messages at an appropriate location, by identifying the gaze direction and then referring to that direction. For example, as shown in FIG. 8, information displayed according to a direction of the user's gaze may be regenerated, and the type and output method of the output information, and the like, may also be varied. More specifically, when the user's gaze is tracked and its direction is determined, a degree of overlap between the corresponding gaze direction and the dangerous path may be recomputed to inform the user of a danger, or a dangerous place that is present in the gaze direction may be displayed on the display, and the information may be controlled to be displayed only in a preset region around the user's gaze direction. That is, the display of the smart glasses may be implemented to display information only in a predetermined region of the display surface along the user's gaze direction, and may have different output forms such as blurring or not displaying the information as a distance from the gaze direction increases. Referring to FIG. 8, (a) of FIG. 8 shows a state in which information is displayed only on a left side surface (D) of the display surface but not displayed on a right-side surface (d) thereof when the user's gaze is directed to the left. In addition, (b) of FIG. 8 shows a state in which information is displayed only surface (D) of the display surface, and the on a central information is not displayed on both end side surfaces (d) thereof where the user is unable to see when the user's gaze is directed to the center.

Furthermore, for reference, although not shown separately in the drawings, a projector laser output device (not shown) may be further provided to display desired information on the display surface of the smart glasses, which is driven according to a control command of the control unit 106 to display various information on the display surface of the smart glasses. In addition, information may be displayed on the display surface of the smart glasses by hologram technology to allow the user to recognize information in three dimensions, and furthermore, components capable of realizing VR and AR may be additionally further provided.

Meanwhile, so far, the description has been given of how a smart device or smart glasses receive infectious disease transmission information from an external server and then display detailed information such as a dangerous path and a dangerous place included therein through a display. However, in general, infectious s disease transmission information that publicly exposed to the outside is often provided only to a very limited extent for the protection of the individual confirmed patient, and for example, as shown in the table shown in FIG. 1, in most cases, only a place where the confirmed patient has stayed and a time of exposure are provided.

However, since this limited information alone may not be sufficient for ordinary citizens to avoid dangerous paths or dangerous places, the system according to the present disclosure may newly generate useful information for actual general users from the limited infectious disease transmission information.

For example, when the infectious disease transmission information including only limited confirmed patient information is initially received or collected, the smart device or service server according to the present disclosure may list a plurality of dangerous places in time sequence and then compute and connect a path between respective dangerous places to ultimately generate a path traveled by the corresponding confirmed patient. That is, in many cases, initial infectious disease transmission information may only provide information on places where the confirmed patient has visited, but does not specifically provide information on how and which road he or she has traveled between places, but the smart device or service server according to the present disclosure may predict a most likely path from the infectious disease transmission information and provide a completed travel path of the confirmed patient. On the other hand, at this time, during a process of computing, by the smart device or service server, to predict a path, information on which path the general users have chosen when traveling between respective places, which means of transportation they have used a lot when traveling, and which path and which means of transportation they have been used for each time period may be referred to, and for example, the information may be cumulatively databased and stored during the past period.

In addition, the smart device or service server according to the present disclosure may be implemented to identify a time period required to travel to a next place and a travel distance to the next place with reference to a time and period stayed at each place, and identify which path and how the confirmed patient has traveled based on the above information. For example, in the table of FIG. 1, it is shown that the confirmed patient visited the OO Mart from 18:05 to 18:27, and then to the oooo restaurant from 18:36 to 18:41 on July 20, and the device or service server according to the present disclosure may compute which means of transportation the confirmed patient used during that time period, and which path he or she traveled with reference to time period information of 9 minutes between 18:27 and 18:36, and distance information from OO Mart to OOOO restaurant.

In addition, the smart device or the service server according to the present disclosure may predict a travel path or a visited place based on limited personal information of the confirmed patient, that is, gender or age group information when computing the travel path of the confirmed patient. Such a prediction computation may also be performed with reference to a database accumulated during the past period.

As such, the smart device or the service server according to the present disclosure may provide infectious disease transmission information to the user at a level of transferring initial information as it is, but on the contrary, may finally generate one completed prediction path and provide it to the user by predicting a travel path where the confirmed patient may have passed, a place where the confirmed patient may have visited, and the like, with reference to the accumulated database. In addition, in a case where the severity of clinical symptoms or infectious disease of each confirmed patient can be classified into numerical values or grades, the user may be allowed to easily recognize a degree of danger by varying the thickness or color of a travel path displayed, the color of a marker indicating a dangerous place, and the radius, size, and color of a mark indicating a dangerous region, such as travel paths of respective confirmed patients, dangerous places, dangerous regions, and the like.

Figure 9:
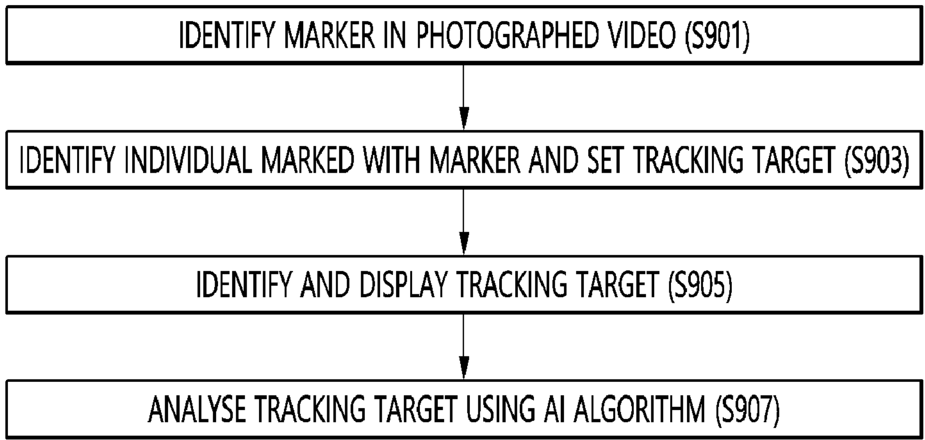
FIG. 9 shows a process in which a method according to a second embodiment of the present disclosure is carried out in sequence.

FIG. 9 shows a process in which a method according to a second embodiment of the present disclosure is carried out in sequence. The second embodiment allows the smart device to track a tracking target marked with a specific marker, for example, to mark a marker that can be recognized by the smart device on a person who has been confirmed, or a suspected livestock determined to have a high body temperature or abnormal behavior pattern, and to display the corresponding individual to be distinguished from other objects on the display when the smart device recognizes the above marker.

Referring to FIG. 9, the second embodiment first starts with identifying, by the smart device, a marker in a video photographed through a photographing unit provided therein (S901). Here, the marker refers to a kind of mark that can be recognized by the smart device, and the above marker may have the form of an arbitrary barcode or two-dimensional code, or may be a paint of a specific color.

Subsequent to step S901, the smart device may fully identify an individual marked with the marker and set the corresponding individual as a tracking target (S903). A computation process of identifying an individual may be carried out through a graphic analysis within a video or image acquired by the photographing unit of the smart device, and during this process, machine learning and deep learning technologies may be used.

Meanwhile, subsequent to step S903, the second embodiment may include displaying the tracking target to be distinguished from other objects in a video acquired through the photographing unit (S905), thereby allowing the user to easily monitor the tracking target.

In addition, subsequent to step S905, the second embodiment may further include inputting various parameters of the tracking target, for example, the tracking target's body temperature, behavior pattern, and other features that can be extracted from the tracking target, acquired by monitoring the tracking target, into an artificial intelligence algorithm to determine or infer the state of the tracking target (S907). Here, the artificial intelligence algorithm may be pre-learned, and in particular, may be pre-learned through learning data in a state in which behavior patterns (lying on one side, lying on one's stomach, rubbing one's body, turning around in place, etc.) of the tracking target and a state of the tracking target are matched.

The foregoing second embodiment may be particularly suitable to carry out infectious disease monitoring for livestock and animals, and for example, an individual showing abnormal symptoms in a pigpen may be marked with a specific marker (paint), and then the user may track and monitor the corresponding individual through a smart device, preferably smart glasses, thereby allowing the user to perform infectious disease monitoring for pigs.

Figure 10:
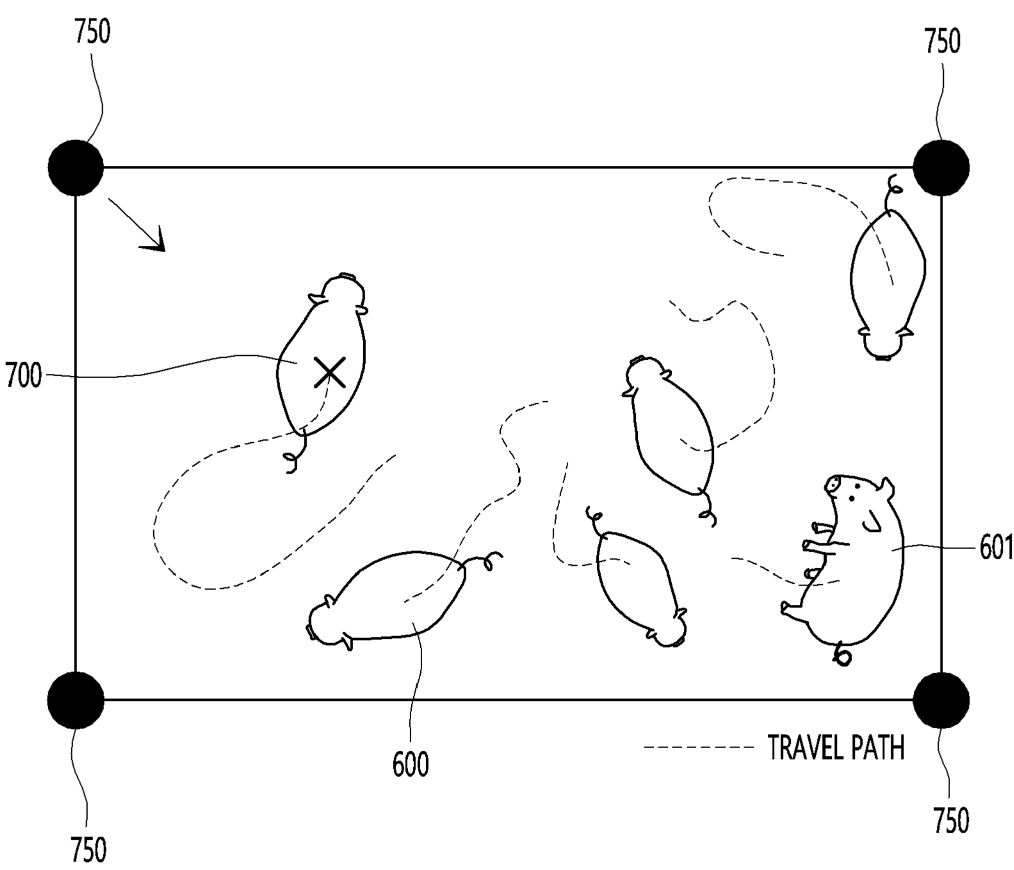
FIG. 10 shows a state in which the second embodiment is implemented in a pigpen as viewed from the top.
Figure 11:
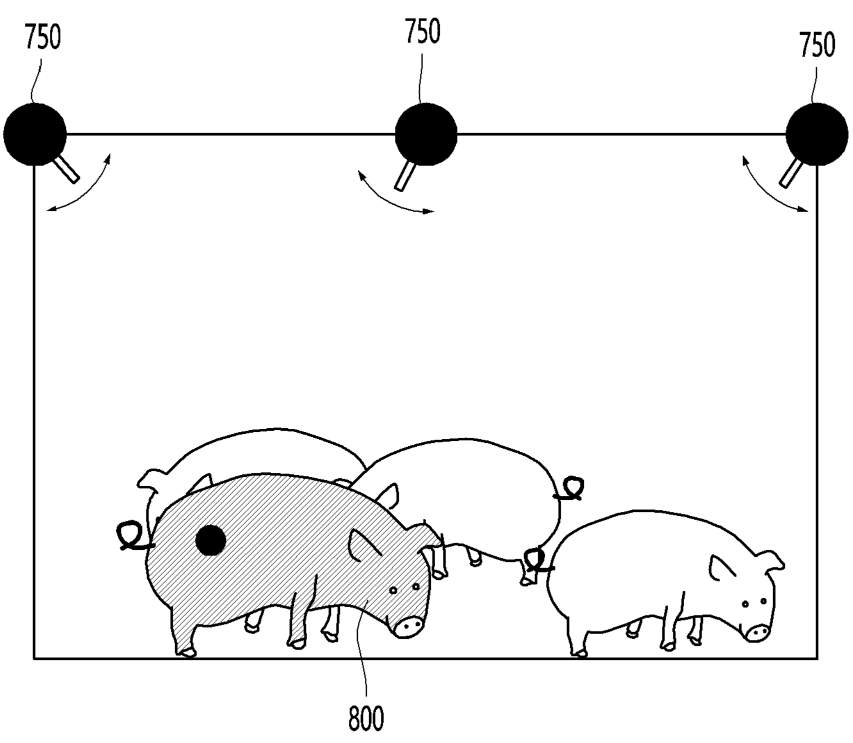
FIG. 11 shows a state as viewed from the side.

FIG. 10 shows a state in which a pigpen is viewed from the top, and FIG. 11 shows a state in which the pigpen is viewed from the side, wherein at least part of a structure of the pigpen may be provided with a means 750 for marking an individual with a marker, for example, a paint gun. The paint gun may be controlled in conjunction with a camera provided in at least part of the structure of the pigpen, and the camera may be implemented as a thermal imaging camera to check a body temperature of each individual pig. As an example, when a specific individual is observed to have abnormally high body temperature, the corresponding individual may be identified by a camera in the pigpen, and the paint gun may fire a marker toward the specified individual 700.

The individual 700 marked with the marker may be set as a tracking target, and then displayed on the display in a conspicuous manner unlike other individuals, as shown in FIG. 10. In addition, the individual set as the tracking target may be displayed with a color on a surface of the individual as shown in reference numeral 800, and thus implemented to continuously perform monitoring even when the field-of-view is covered by other individuals, as shown in FIG. 11.

On the other hand, the travel paths of respective individuals within the pigpen may be displayed as a set of arbitrary consecutive dots as shown in FIG. 10. The travel path of the tracking target may be displayed as a solid line in some cases. The record of such a travel path may be used for the purpose of identifying the behavior patterns of individuals, and the travel path may be stored in conjunction with time information, thereby identifying whether they have been in contact with a specific tracking target. That is, the travel path of the tracking target may be compared with that of an arbitrary individual, thereby identifying whether the tracking target has been able to transfer a causative agent of the infectious disease to the arbitrary individual. For reference, an individual having reference numeral 600 indicates an individual with no special symptoms, an individual having reference numeral 601 indicates a suspected individual in an abnormal state due to lying on one side with little movement on the bottom of the pigpen (or in an abnormal state due to lying on one's stomach, or sitting), and an individual having reference numeral 700 indicates an individual marked with a marker as a high body temperature has been measured.

A method of providing information for infectious diseases monitoring using a smart device and a system for the same have been described above. Meanwhile, the present disclosure is not limited to specific embodiments and application examples described above, and various modifications may of course be carried out by those skilled in the art to which the invention pertains without departing from the gist of the present disclosure claimed in the claims, and those modifications should not be understood separately from the technical concept and prospect of the present disclosure.

The invention claimed is:

1. A method of providing information for infectious disease monitoring using a smart device, the method comprising:

receiving, by a communication unit of the smart device, infectious disease transmission information from a service server;

acquiring, by a location identification unit of the smart device, current location information of the smart device;

displaying at least one of a dangerous path or a dangerous location included in the infectious disease transmission information through a display provided in the smart device with reference to the acquired current location information; and comparing the current location information with the infectious disease transmission information to output a notification to a user, wherein the smart device is smart glasses comprising a photographing unit and a gaze sensor, wherein the dangerous path comprises a travel path of a confirmed patient or a travel path of another user who has traveled on a path at least part of which overlaps the travel path of the confirmed patient, and wherein outputting the notification comprises:

(i) identifying an avoidance path for avoiding the dangerous path or the dangerous location based on the current location information;

(ii) overlaying the identified dangerous path and the avoidance path on a real-time video photographed through the photographing unit; and (iii) dynamically adjusting an output position of the dangerous path and the avoidance path on the display based on a user's gaze direction tracked by the gaze sensor, such that the avoidance path is prioritized within a center of the user's vision when it is detected that the user's gaze direction overlaps the dangerous path.

2. The method of claim 1, wherein the smart device receives infectious disease transmission information at preset time intervals from the service server to update the dangerous path and the avoidance path in real time based on changes in the current location information.

3. The method of claim 1, wherein the smart glasses further comprise a gaze sensor that tracks a user's gaze, and wherein the smart glasses output a predetermined notification in the form of a visual alert overlapping the center of the user's vision when it is detected that the user's gaze is directed toward a front center thereof.

4. The method of claim 1, wherein the outputting through the display comprises:

(i) recognizing a sidewalk or a road within the video photographed through the photographing unit;

(ii) rendering the dangerous path and the bypass route as three-dimensional (3D) augmented reality (AR) objects aligned with the recognized sidewalk or road; and (iii) varying a visual transparency or a blur level of the rendered objects based on a distance from the user's gaze direction to the dangerous path.

5. The method of claim 4, wherein the dangerous path is generated by the smart glasses or the service server by predicting a most likely path between visited places of the confirmed patient using a database of transportation means and travel times accumulated over a past period.

6. The method of claim 1, wherein the notification varies at least one of a color, a thickness, or a vibration intensity of the output method thereof according to a distance from the dangerous path or dangerous place based on current location to induce the user to move away from a dangerous source.

* * * * *